(12) United States Patent
Mohr

(10) Patent No.: US 7,507,975 B2
(45) Date of Patent: Mar. 24, 2009

(54) SYSTEM AND METHOD FOR HIGH RESOLUTION RADIATION FIELD SHAPING

(75) Inventor: Stephen Mohr, Danville, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 92 days.

(21) Appl. No.: 11/589,415

(22) Filed: Oct. 30, 2006

(65) Prior Publication Data

US 2008/0073591 A1 Mar. 27, 2008

Related U.S. Application Data

(60) Provisional application No. 60/793,907, filed on Apr. 21, 2006.

(51) Int. Cl.
*A61N 5/10* (2006.01)
(52) U.S. Cl. .............. 250/492.1; 250/505.1; 250/492.3; 378/65; 378/145; 378/147; 378/150; 378/152
(58) Field of Classification Search .............. 250/492.1, 250/505.1, 492.3; 378/65, 145, 147, 150, 378/152
See application file for complete search history.

(56) References Cited

U.S. PATENT DOCUMENTS

| | | | | |
|---|---|---|---|---|
| 4,868,844 | A * | 9/1989 | Nunan | 378/152 |
| 5,012,506 | A | 4/1991 | Span et al. | 378/152 |
| 5,166,531 | A | 11/1992 | Huntzinger | 250/505.1 |
| 5,438,454 | A * | 8/1995 | Ludewigt et al. | 359/641 |
| 5,555,283 | A * | 9/1996 | Shiu et al. | 378/151 |
| 5,591,983 | A * | 1/1997 | Yao | 250/505.1 |
| 5,757,881 | A | 5/1998 | Hughes | 378/65 |
| 6,052,430 | A | 4/2000 | Siochi et al. | 378/65 |
| 6,052,436 | A | 4/2000 | Huttner et al. | 378/152 |
| 6,266,393 | B1 * | 7/2001 | Ein-Gal | 378/152 |
| 6,314,159 | B1 * | 11/2001 | Siochi | 378/65 |
| 6,322,249 | B1 | 11/2001 | Wofford et al. | 378/207 |
| 6,388,816 | B2 | 5/2002 | Brown et al. | 359/641 |
| 6,459,769 | B1 * | 10/2002 | Cosman | 378/147 |
| 6,600,810 | B1 * | 7/2003 | Hughes | 378/152 |
| 6,730,924 | B1 | 5/2004 | Pastyr et al. | 250/505.1 |

(Continued)

OTHER PUBLICATIONS

Xia, et al ("Physical Characteristics of a miniature multileaf collector," Med. Phys. 26 (1) Jan. 1999, pp. 65-71).*

(Continued)

*Primary Examiner*—Jack I Berman
*Assistant Examiner*—Michael Maskell
(74) *Attorney, Agent, or Firm*—Houst Consulting

(57) ABSTRACT

A system and method are provided for a high resolution radiation treatment system which provide for projecting a field of radiation energy at targeted patient tissue. The system uses a multi-leaf collimator, which is positioned such that a significant clearance is provided between the multi-leaf collimator and the isocenter plane where the targeted tissue is located. The leaves of the multi-leaf collimator are designed to provide for high step resolution in the projected radiation energy shape. Additionally, an embodiment of the system and method herein can provide for a high step resolution in the projected radiation energy shape, and for a dose calculation matrix which has matrix units which coincide with the high step resolution in the projected radiation shape.

34 Claims, 12 Drawing Sheets

U.S. PATENT DOCUMENTS

| | | | | |
|---|---|---|---|---|
| 6,853,705 | B2* | 2/2005 | Chang | 378/65 |
| 6,891,178 | B2 | 5/2005 | Xing | 250/505.1 |
| 7,221,733 | B1* | 5/2007 | Takai et al. | 378/65 |
| 7,295,649 | B2* | 11/2007 | Johnsen | 378/65 |
| 2003/0072410 | A1* | 4/2003 | Siochi | 378/65 |
| 2004/0184579 | A1* | 9/2004 | Mihara et al. | 378/65 |
| 2005/0254623 | A1* | 11/2005 | Kamath et al. | 378/65 |
| 2007/0071168 | A1* | 3/2007 | Allison et al. | 378/65 |

OTHER PUBLICATIONS

Bortfeld, et al ("What is the optimum leaf width of a multileaf collimator?" Med. Phys. 27 (11) Nov. 2000, pp. 2494-2503).*

Low, et al. ("Characterization of a commercial multileaf collimator" Med. Phys. 28 (5) May 2001, pp. 751-756.).*

Millenium MLC Multileaf Collimator, Varian Medical Systems, 10 pages, 2001.

44th AAPM Annual Meeting, Montreal 2002, Treatment Delivery Systems 2, Field Shaping; Design Characteristics and Dosimetry Issues, by Timothy D. Solberg, 20 pages, 2002.

Stereotactic Radiotherapy Brings New Hope, Centerline, Oct. 2005, by Nancy Heifferon, 5 pages.

Xia, et al. ("Physical Characteristics of a miniature multileaf collector," Med. Phys. 26(1) Jan. 1999, pp. 65-71.

Bortfeld, et al. ("What is the optimum leaf width of a multileaf collimator?" Med. Phys. 27 (11) Nov. 2000, pp. 2494-2503.

* cited by examiner

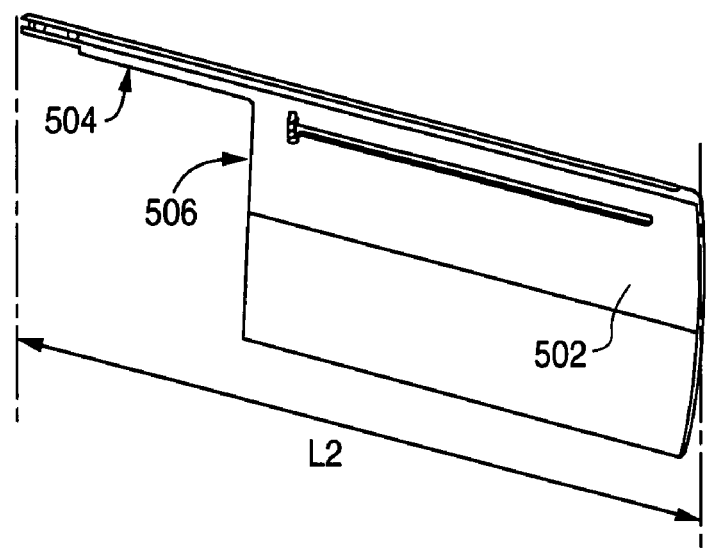
FIG. 5A
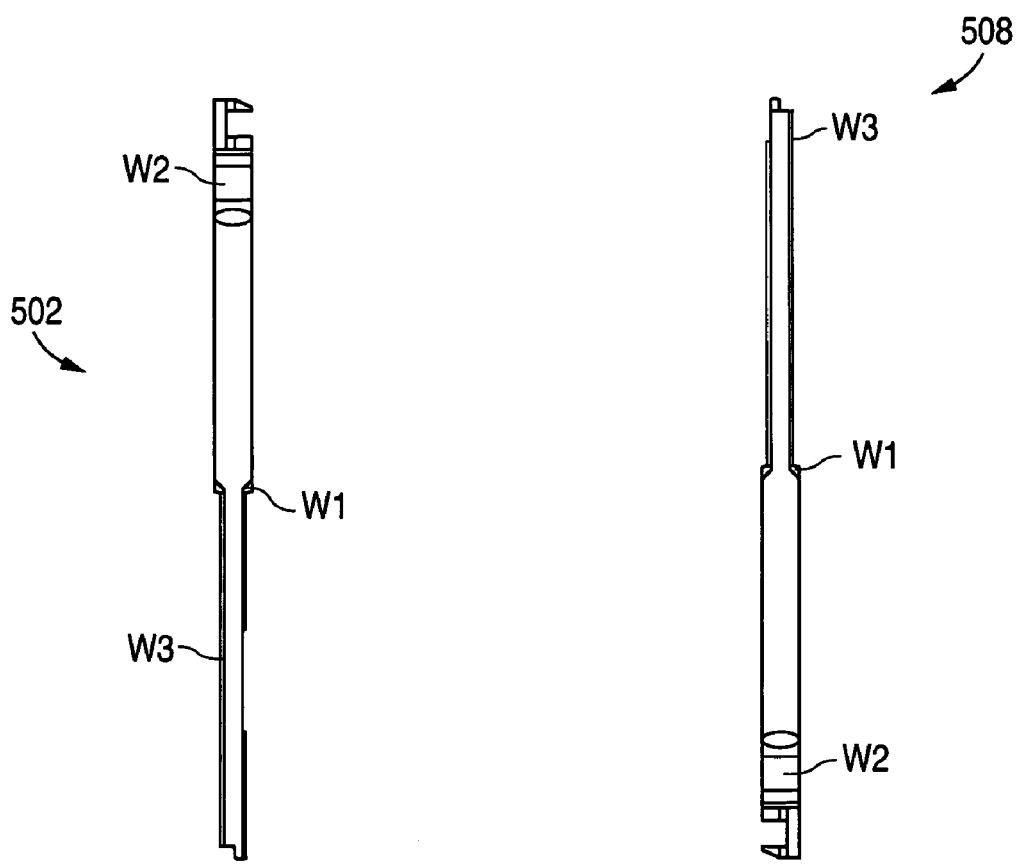
FIG. 5B        FIG. 5C

SYSTEM AND METHOD FOR HIGH RESOLUTION RADIATION FIELD SHAPING

RELATED APPLICATION

This patent application claims the benefit of U.S. Provisional Application No. 60/793,907, filed Apr. 21, 2006, entitled SYSTEM AND METHOD FOR HIGH RESOLUTION FIELD SHAPING which is incorporated herein by reference.

FIELD OF THE INVENTION

This present application relates to a system and method for shaping a projected radiation field such that it can be used to provide medical treatments.

BACKGROUND

Use of radiation therapy to treat tumors, and possibly other areas of targeted tissue, is widely known. There are a number of challenges associated with using radiation to treat targeted areas of tissue in a patient's body. One challenge is identifying the location of the volume of tissue in the patient's body which is targeted for treatment. Another challenge is shaping the radiation field so that the radiation field directed to the patient's body conforms to the area of tissue which is identified for treatment.

A number of different techniques can be used to control the shape of the radiation field which is directed the targeted area of the patient's tissue. One widely used device for controlling the shape of the radiation field is a multi-leaf collimator, which may be referred to at points herein as a MLC for ease of reference.

Previous MLCs have been provided in a wide range of different designs, and generally utilize a number of movable leaves which interposed in the path of radiation, to block a portion of the radiation emitted by a radiation source, and the unblocked radiation forms a radiation field shape which is then incident at an isocenter plane. One example of a prior MLC is shown in U.S. Pat. No. 5,166,531, entitled LEAF-END CONFIGURATION FOR MULTI-LEAF COLLIMATOR, which is assigned to the same assignee as the present application, and which is incorporated herein by reference. Additional aspects of other examples of MLC implementations are shown in U.S. Pat. Nos. 6,891,178; 5,012,506; and 6,600,810, each of which are incorporated herein by reference.

In operation a radiation treatment system using an MLC is designed to balance a number of competing factors in order to provide a combination of characteristics which will provide a tool which medical personnel can use to provide a patient with effective and efficient targeted and controlled radiation treatment.

BRIEF DESCRIPTION OF DRAWINGS

FIGS. 5A-5C show different views of leaves of an MLC of the present invention.

DETAILED DESCRIPTION

Figure 1A:
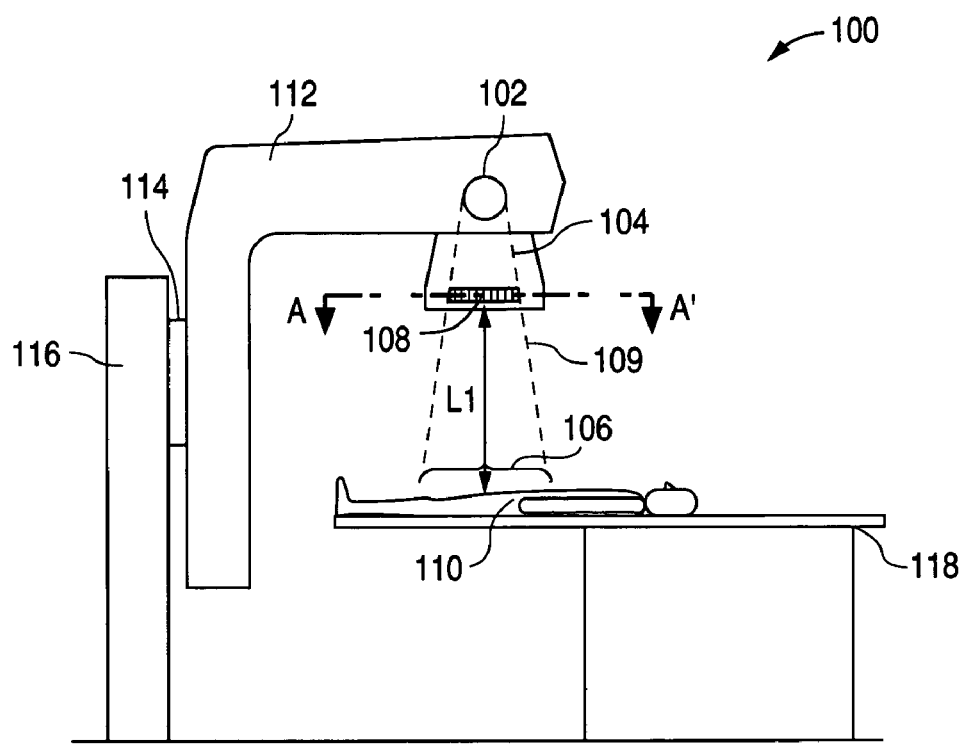
FIGS. 1A-1D show different views of embodiments of radiation treatment systems of the present invention.

The basic layout of a radiation treatment system 100 of an embodiment herein is illustrated in FIG. 1A. FIG. 1A provides a radiation source 102 which emits radiation energy 104. As used herein radiation energy should be interpreted to include a range of different types of energy which is used to apply a medical treatment to a patient's tissue, including for example photon radiation, and proton radiation, and other possible types of radiation. The radiation energy 104 spreads out as it travels away from the radiation source 102. The radiation source 102 can be disposed in a support arm. In many systems the support arm 112, which is sometimes referred to as a gantry, will be mounted to gantry bearing 114, which provides rotatable member coupling the gantry to stand 116 which operates as fixed support structure. The gantry bearing 114 allows the gantry 112 which supports the radiation source 102 and the MLC to be rotated around the patient so as to allow for targeting the radiation field toward different areas of tissue for treatment. The gantry 112 can be formed of metal, or other structurally supportive materials, and included in the gantry can be various control lines, and power lines which operate to provide power and control to various elements, such as the MLC 108, and the radiation source 102 which are coupled in the gantry 112.

The patient 110 is secured to a patient support assembly table 118, which is movable such that the targeted tissue of the patient can be positioned at an isocenter of the radiation energy 104. The shape of the radiation energy which is projected onto an area 106 the patient's body is then controlled using a multi-leaf collimator 108. In one embodiment the MLC is positioned between the radiation source 102 and the isocenter, such that there is a clearance distance L1 of at least approximately 400 mm or more between the isocenter and the side of the MLC which is closest to the isocenter.

An embodiment of the system herein provides for among other things a high resolution multi-leaf collimator, which can provide for leaves of the multiple leaf collimator that project a shape step resolution size of about 3 mm or less at the isocenter. One embodiment of a system herein would provide for a radiation source 102 as shown in FIG. 1. In one embodiment the distance between the source and the patient would be in the range of approximately 800-1000 mm. In one embodiment with a source at a distance of 1000 mm from the isocenter, the distance between a horizontal centerline of the MLC 108 and the radiation source is provided at 510 mm. Thus, there is a distance of 490 mm between the horizontal centerline of the MLC and the isocenter. The radiation energy 104 is projected through the MLC 108, and the position of the leaves of the MLC can be adjusted to control the shape, or pattern, of the radiation which is projected onto the patient, and the shape at the isocenter.

Figure 1B:
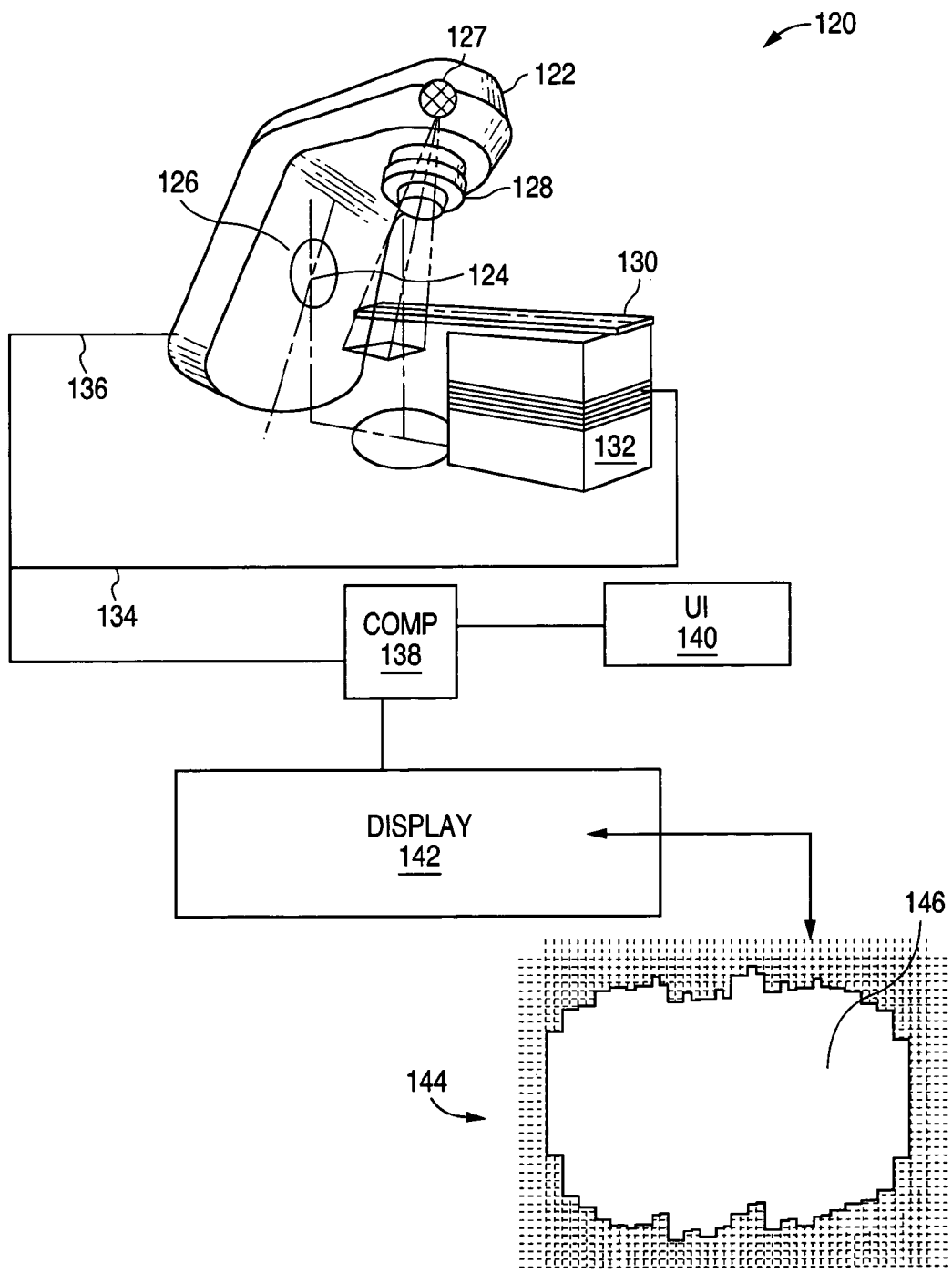

FIG. 1B shows another view of an embodiment of a radiation treatment system 120. The illustration of system 120 shown in FIG. 1B shows a gantry 122, which operates as a support arm, which has been rotated slightly on the axis 124 of a gantry bearing 126. The radiation source 127 emits radiation through the MLC and other radiation field shaping elements contained an beam shaping housing 128 also referred to as collimator cover, coupled to the gantry 122. The system 120 includes a patient support assembly table 130 with controllable height adjustment of the patient support assembly 132, which allows for positioning the tissue to be treated at the isocenter of the radiation treatment system. Control lines 134 and 136 couple the controllable height adjustment support 132, and the gantry 122, and the elements which are contained in, or coupled to the gantry, with a computer 138, and a printer could be included for printing information and images generated by the computer. The computer 138 is shown as a single computer where such a computer could be standard PC programmed to control the operations of the various elements of the system; in some embodiments the computer could be implemented as multiple computers, or processors which could be provided for at various location in the radiation system, or located remotely from the radiation system, but communicatively coupled with various elements of the system. The computer 138 then controls various elements of the system to provide the prescribed radiation treatment to a patient. The computer can be a standard personal computer, or other computer system, which is programmed to interface with the components of the radiation treatment system. The computer 138 could be coupled with user interface devices 140, such as a mouse, and a keyboard. Information, and images could be presented to a user by a display 142 coupled to the computer 138. For example, in one embodiment a processor of the computer will be programmed such that the display will operate to show an image 144 having a dosimetry matrix, also referred to as a dose calculation matrix, with grid line units, where the grid line units have a length which corresponds to a length of 0.3 mm or less for a projected radiation image at the isocenter, and the image 144 can include a corresponding radiation shape image which will correspond with the radiation image projected at the isocenter where the tissue to be treated is positioned, wherein at least a portion of the projected image at the isocenter will have a step resolution which corresponds to the length of the units of the dosimetry matrix. The relationship between the projected radiation field shape and the dosimetry matrix will be discussed in greater detail below. The computer 138 will, via the control line 136, which can include multiple control lines, control the position of the leaves of the MLC to provide for a projected radiation field shape at the isocenter which will correspond to the radiation field shape 146 shown in the image 144. In one embodiment, a user of the system will be provided with input controls through the computer 138 such that user can control the positioning of the MLC leaves to provide a radiation shape which will correspond to the area of tissue selected for treatment.

Figure 1C:
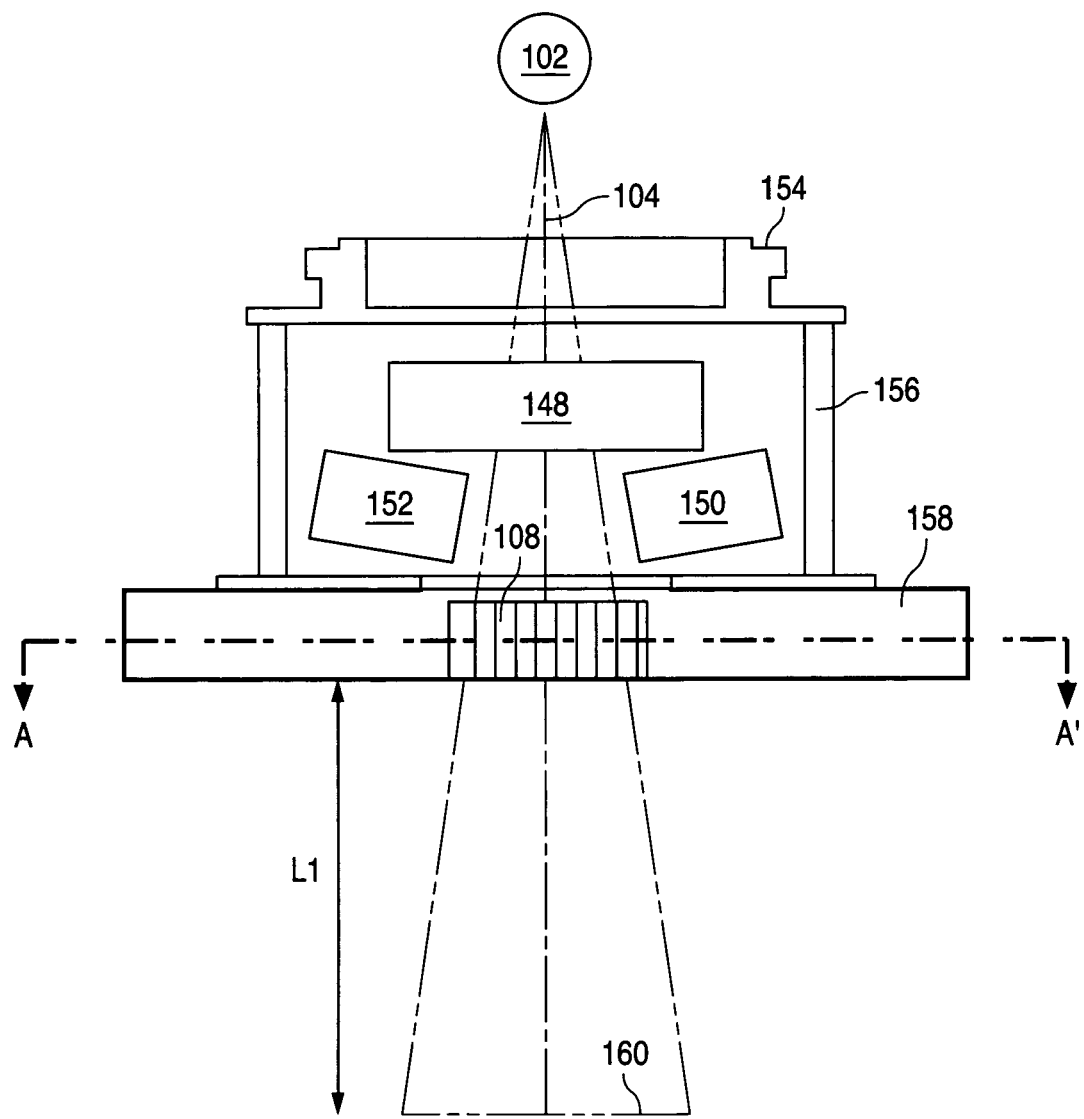

FIG. 1C shows a cross sectional view taken through the collimator cover 128 and shows beam shaping components contained in the collimator cover. Annular support structures 154 and 156 provide for the lateral sides of the collimator cover, and provide lateral structural support for upper jaw components 148 and another upper jaw not shown. These support structures 154 and 156 can be composed of metal or structural synthetic materials. The source 102 emits the radiation field 104 which is transmitted through a first beam shaping area where upper jaw components 148 operate to provide lateral side shaping of the emitted radiation energy 104. The emitted radiation energy then passes through a second beam shaping area where lower jaw components 150 and 152 provide additional lateral side shaping to the radiation energy. The radiation energy 104 then passes through the MLC 108 which is disposed in support structure 158. The leaves of the MLC are then positioned to provide specific shaping to the radiation energy so as to provide a projected radiation energy shape at the isocenter 160 which corresponds to the targeted area of tissue to be exposed to the radiation energy. The isocenter 160 can be a plane which is at a predetermined distance from the energy source 102. The radiation treatment system is configured and calibrated such that it provides a known, and controllable amount of energy at the isocenter 160. Also the MLC 108 is at fixed distance of the from the isocenter, so the positioning of the leaves of the MLC will result in specific projected radiation energy shapes, where the projected shape of the radiation is a function of both thickness of the leaves of the MLC and the distance of the leaves of the MLC from the isocenter.

FIG. 1C also shows the clearance distance L1 between the bottom of the MLC and the isocenter 160. In one embodiment this clearance distance will be approximately 415 mm, and this clearance distance could be greater, or somewhat less. However, ideally this clearance distance would not be less than 400 mm. It should be noted that the clearance L1 between the bottom of the MLC 108 and the isocenter 160 as shown in FIG. 1C is substantially the same as the clearance between the bottom most part of the support structure 158 and the isocenter. However, in many embodiments the support structure 158 of other elements of the system might extend further toward the isocenter. As discussed herein clearance, unless otherwise specified will be a reference to the distance between the bottom MLC and the isocenter. In different embodiments of radiation system of the present invention different implementations of the collimator cover 128 and the support structure and other elements of the system may extend beyond the bottom most portion of the MLC and thus be closer to the isocenter. However, regardless of the position of the various supporting elements the bottom of the MLC can operate to determine an important clearance parameter in that clearance cannot be greater than distance between the bottom of the MLC and the isocenter.

This clearance distance between the MLC and the isocenter provided for by an embodiment of the system herein is such that even where elements of the collimator cover or other elements of the system extend beyond the bottom of the MLC, the system still provides sufficient clearance such that a wide range of patients will be able to be treated in the system. In some prior radiation treatment system the amount of clearance between the isocenter and the bottom of the MLC, or the housing supporting the MLC, was not great enough to accommodate very large patients, for example when a targeted tumor was located at a deep level in patient's tissue. Thus, when the targeted tissue was positioned at the isocenter the upper area of the patient's body might actually protrude against the MLC or the housing supporting the MLC. Indeed, in such cases the radiation treatment system could likely not be used to treat the patient. In most cases, however, a clearance of 400 mm or more will be suitable to provide treatment.

Figure 1D:
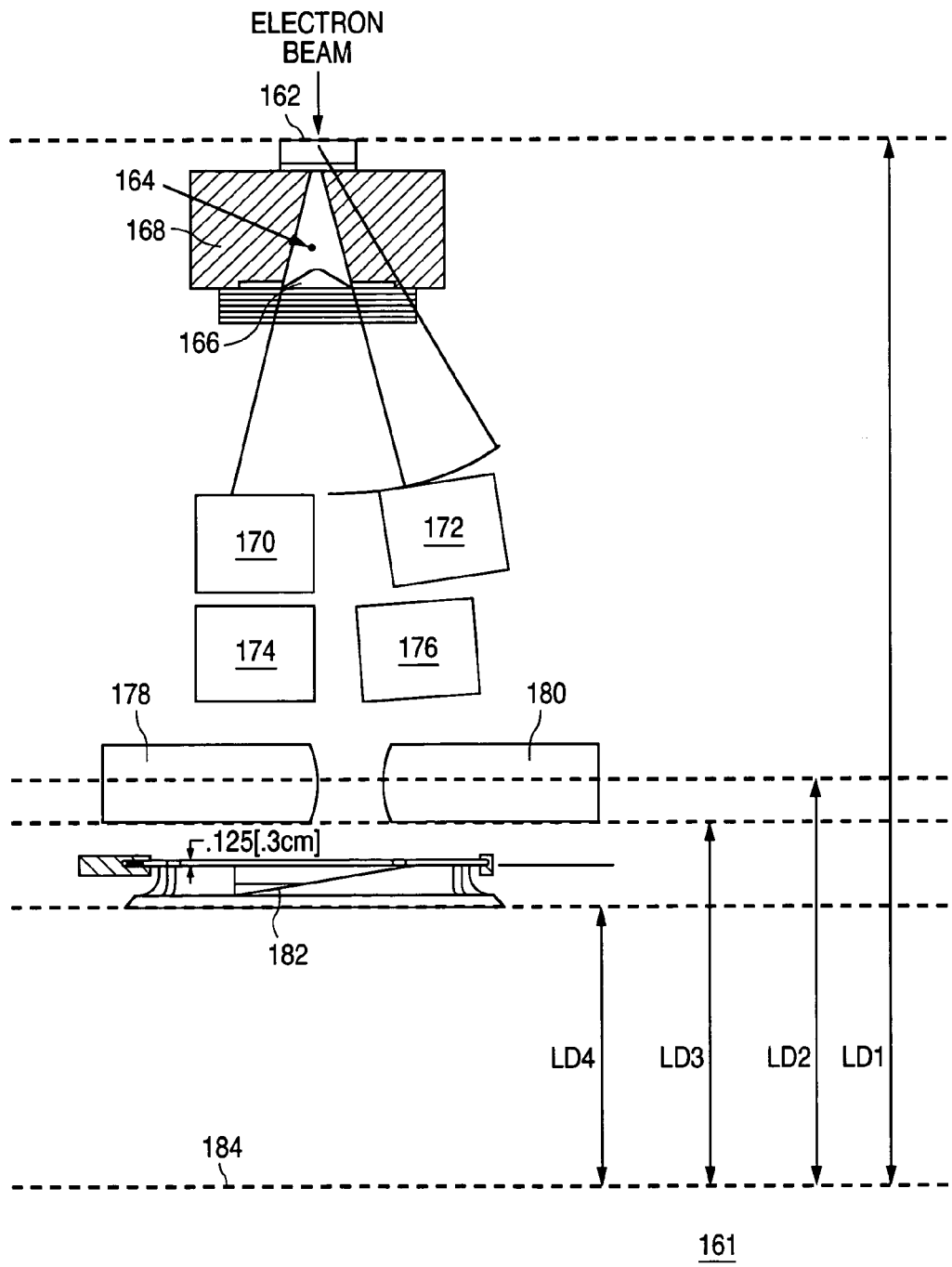

FIG. 1D shows additional aspects of an embodiment of a radiation system 161 of the present invention. The system provides for a source where an electron beam is transmitted into a target 162. The target can be comprised of tungsten. A primary collimator 168 is provided which operates to collimate the radiation. An open area 164 within the primary collimator provides for a transmission path for the radiation beam. A filter 166 operates to evenly distribute the energy of the radiation beam. Upper Jaws 170 and 172, and lower jaws 174 and 176 operate to further shape the radiation beam. In FIG. 1D the position of the lower jaws 174 and 176 has been rotated by 90 degrees for illustrative purposes. The MLC leaves 178 and 180 are then positioned between the lower jaws 174 and 176, and the isocenter plane 184. FIG. 1D does not show the collimator cover and other structural elements of the radiation system 161. In one embodiment the collimator cover would provide a mounting bracket where an upper wedge compensator 182 could be positioned between the MLC leaves and the isocenter plane. In some embodiments additional beam conditioning elements could also be provided for between the MLC and the isocenter plane 184. In one embodiment the distance between the source and the isocenter LD1 is approximately 1000 mm or greater. The distance LD2 between the horizontal centerline of the MLC leaves 178 and 180 and the isocenter plane 184 is approximately 490 mm. The clearance distance LD3 between the bottom of the MLC leaves 178 and 180 is approximately 458 mm. The distance LD4 between the bottom of the upper wedge compensator 182 and the isocenter is approximately 426 mm. It should be noted that the basic configuration of elements shown in FIG. 1D has been used in prior art radiation systems. However the radiation system 161 is unique in part because the clearance LD3 between the bottom of the MLC and the isocenter, and the configuration of the leaves of the MLC provide for a unique combination of substantial clearance between the MLC and the isocenter and a step resolution of approximately 3 mm or less.

Figure 2:
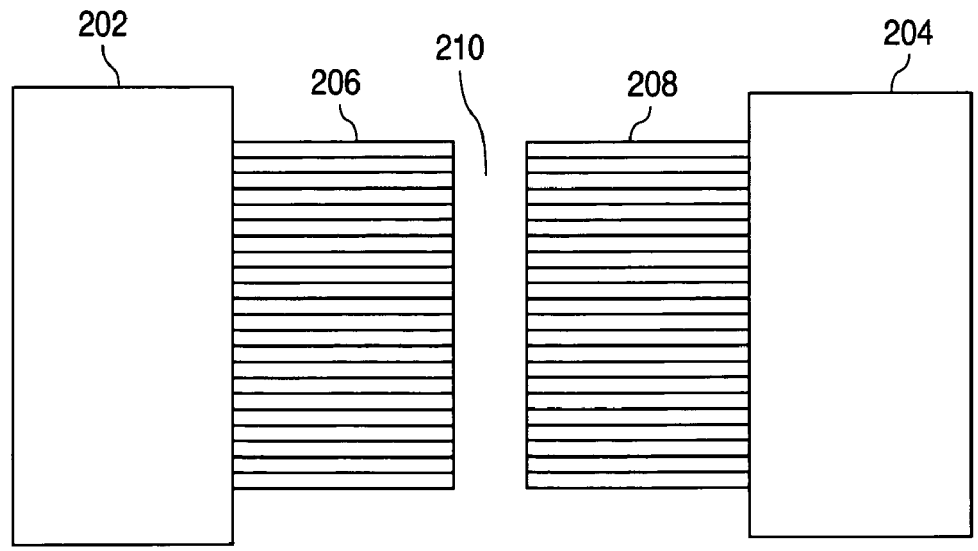
FIG. 2 shows a simplified cross sectional view of a multi-leaf collimator.

FIG. 2 is a simplified cross sectional view taken along A-A' as shown in FIGS. 1A and 1C, which illustrates the basic configuration of an MLC 108. The simplified view of the MLC 108 shown in FIG. 2 shows a number of the basic elements of the MLC. The MLC includes two opposing support carriages 202 and 204. In one embodiment each of these support carriages are made of single piece of machined metal. Each support carriage secures a set of multiple leaves. The position of the set of leaves 206 can be individually controlled by drive motors secured to the housing support structure 202, and similarly the position of the leaves 208 can be controlled by motors secured to the housing support structure 204, where these motors receive control signals from the computer 138. The position of the leaves 206 and 208 as shown in FIG. 2 is not representative of a likely treatment configuration but is provided for illustrative purposes. In the position shown in FIG. 2, the radiation source, which would be positioned directly above the MLC, would emit radiation energy, and a portion of the energy would be blocked by the leaves 206 and 208, and a portion of the energy would pass through the gap 210 between the leaves 206 and 208. This energy passing through the gap 210 would then be incident on a generally rectangular area of the patient's tissue located at the isocenter. The position of the leaves of the MLC 108 can be controlled to provide for a wide range of different field shapes to provide treatment to wide variety of different selected areas of treatment, which can allow, for example, for applying radiation to a wide range of different shaped tumors located in patient.

Figure 3A:
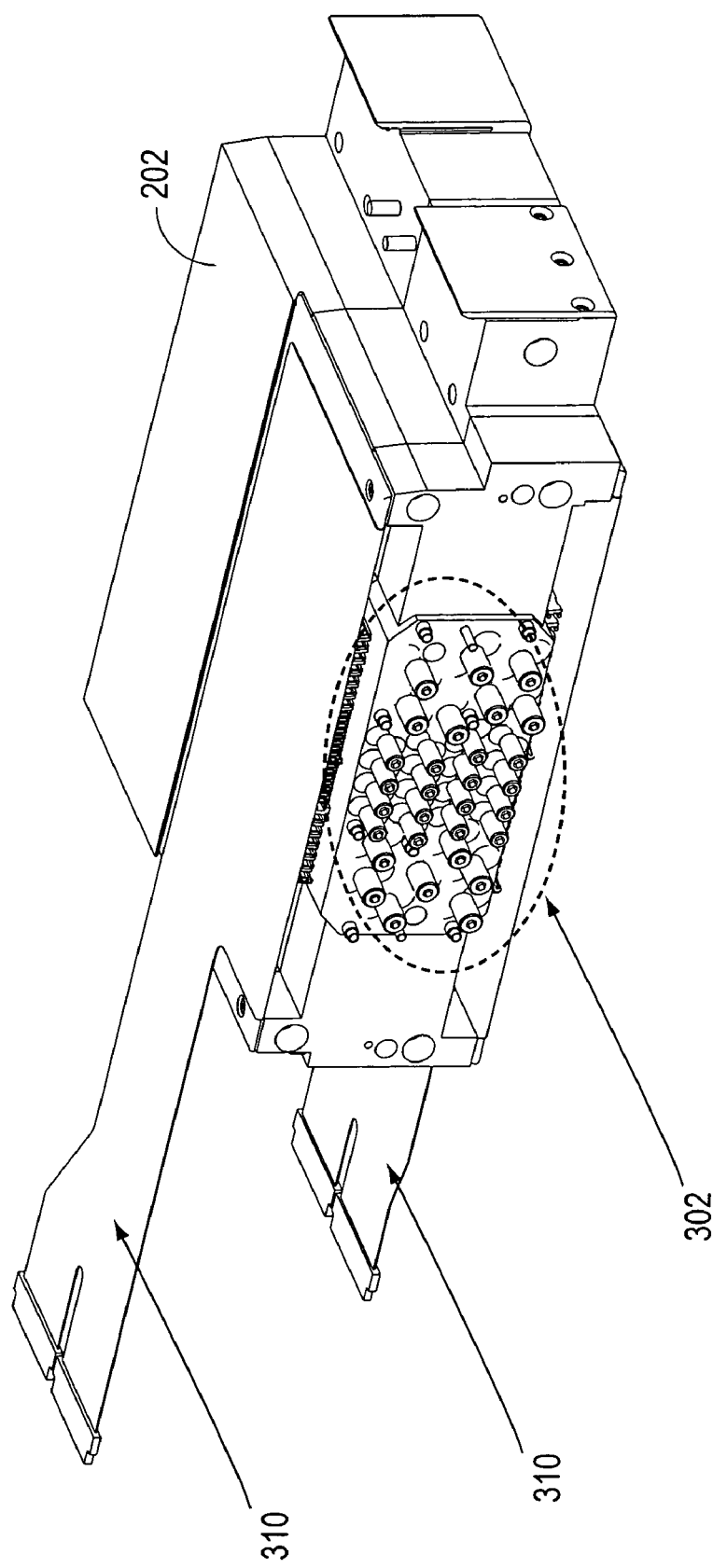
FIGS. 3A-3B show isometric views of one half of a multi-leaf collimator of the present invention.
Figure 3B:
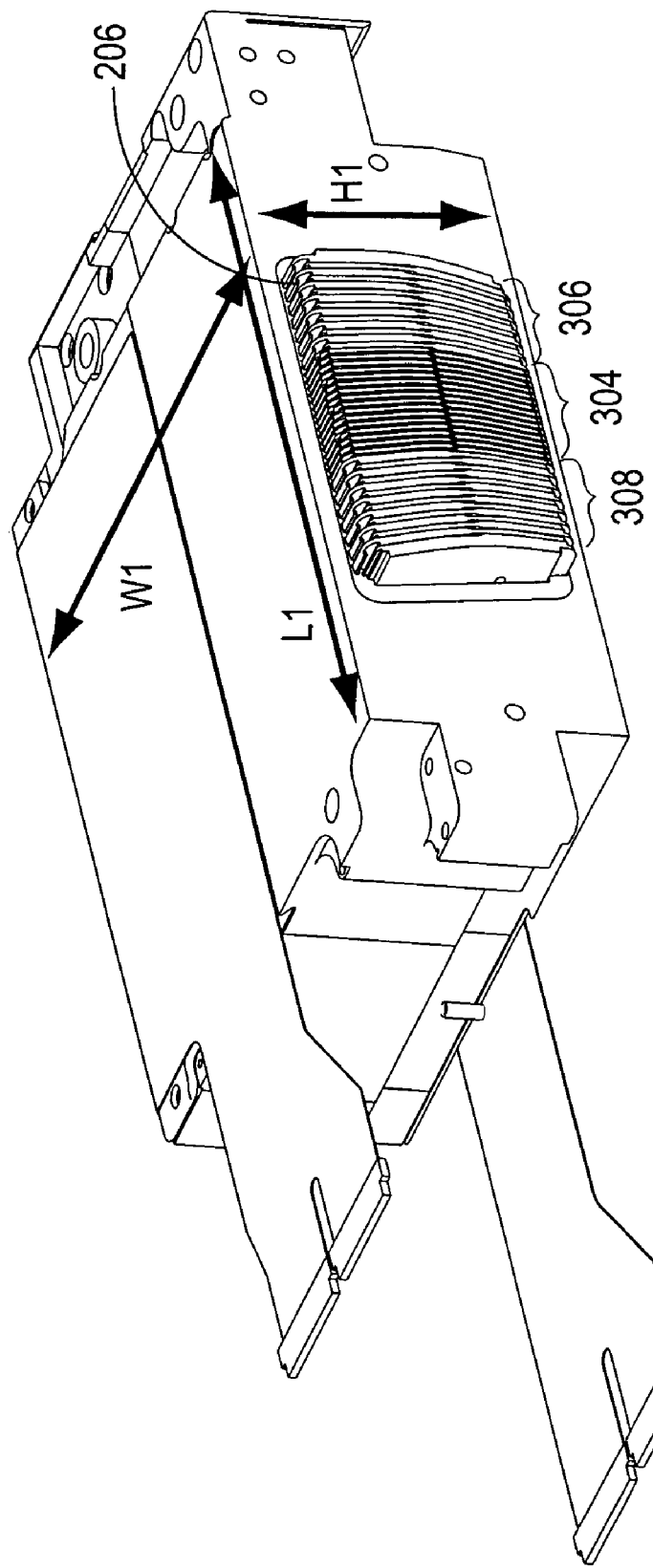

FIGS. 3A and 3B show different views of the support carriage 202 and the leaves 206 for one half of the MLC 108. FIGS. 3A and 3B also show additional elements of the MLC. In one embodiment the width W1 of the support carriage is about 300 mm; the length L1 of the support carriage is about 240 mm; the height H1 of the support carriage is about 85 mm.

FIG. 3A shows a number of very small high precision screw motors in area 302. Each of the screw motors is coupled with one of the individual leaves of the set of leaves 206. The individual screw motors can be controlled to cause the leaf to which the motor is coupled to either project outward from the support carriage 202, or retract into the support carriage 202. In one embodiment the set of leaves 206 of the MLC can include different types of leaves. The regions 306 and 308 of the leaves 206, are lower resolution leaves which have in one embodiment a transitional thickness in the general range of approximately 0.25 cm, which corresponds to a projected step resolution on the patient's tissue of approximately 0.5 cm. The leaves in the region 304 are higher resolution leaves having a transitional thickness in the general range of approximately 0.125 cm, which corresponds to a projected step resolution on the patient's tissue of approximately 0.25 cm, in an embodiment where the source is approximately 1000 mm from the isocenter and the MLC is located about 500 mm away from the source. The transitional thickness refers to a center area of the leaf where the thickness of the leaf is changing from a thicker portion of the leaf to a thinner portion of the leave as is described in more detail below.

Figure 4A:
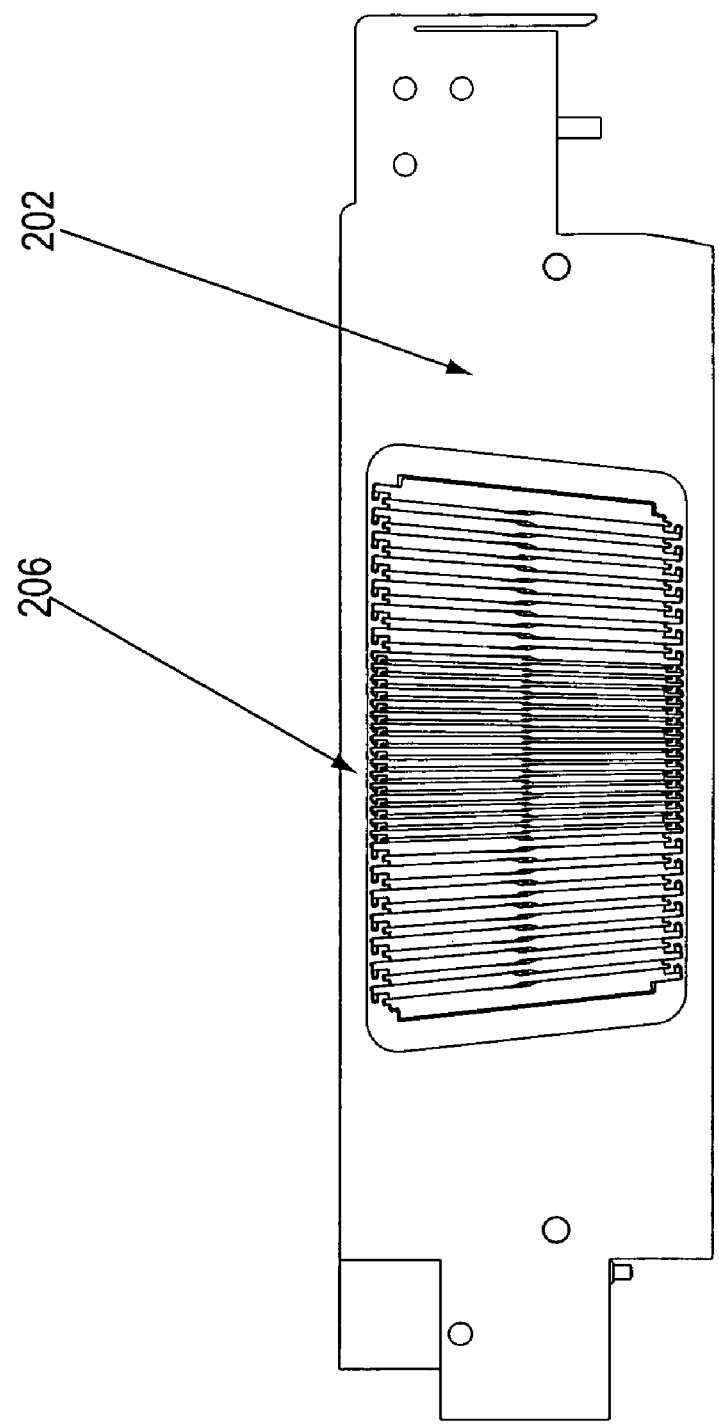
FIGS. 4A-4B show side views of multi-leaf collimator of the present invention.
Figure 4B:
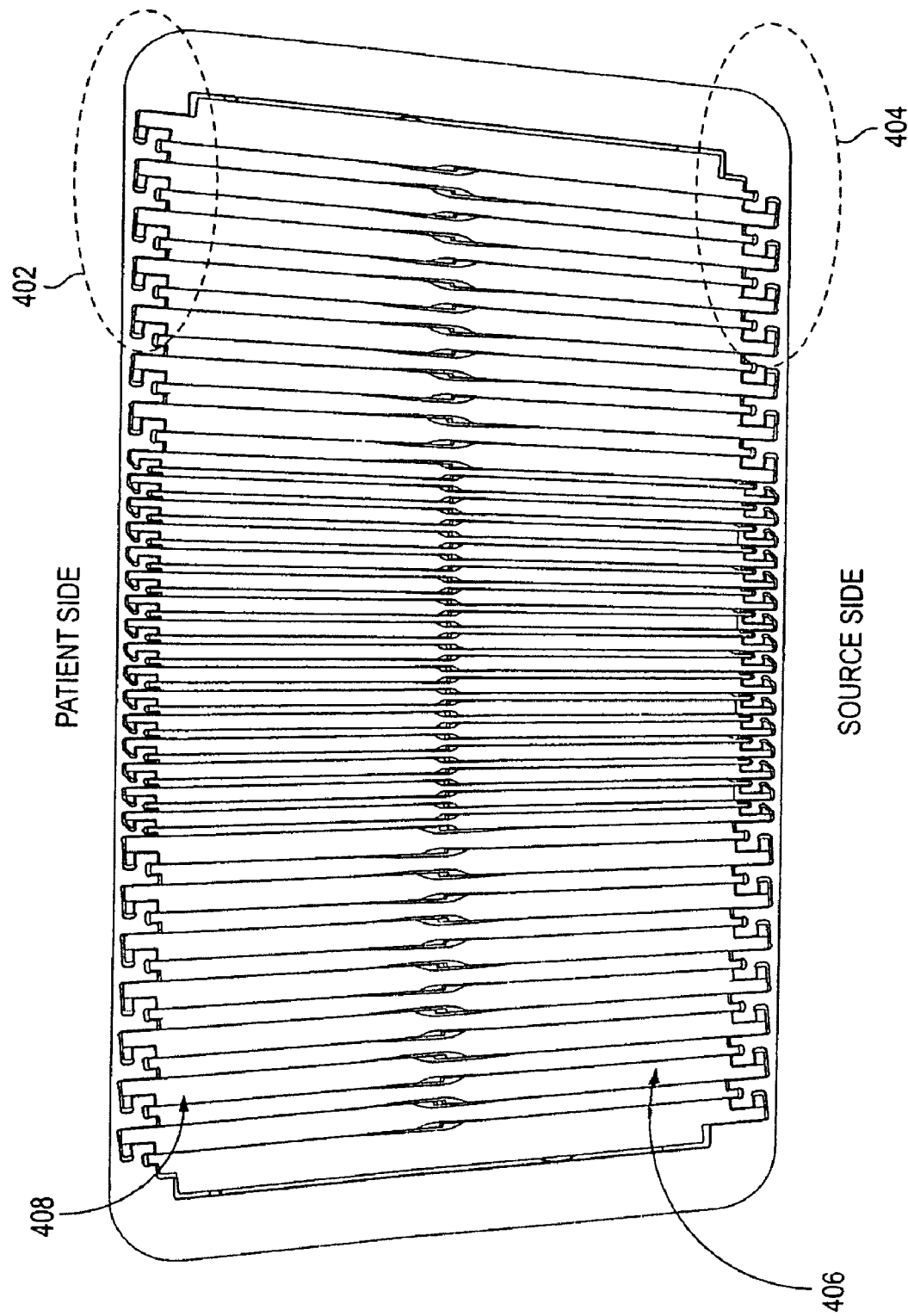

FIGS. 4A and 4B illustrate additional views of the support carriage 202 and the set of leaves 206. The area 402 and the area 404 illustrate a hook and tab sliding coupling between the support carriage and the leaf. This hook and tab arrangement is advantageous because it distributes the friction and contact wear and tear between the leaves and the support carriage along both the top edge and the bottom edge of the leaf, and this configuration will substantially increase the usable life of the MLC. Additionally, the coupling of the leaves at the top and bottom edge of the leaf to the support carriage via the hook and tab arrangement serves to reduce system noise. It should be noted that as shown clearly in FIG. 4B the leaves can be composed of two sections with narrow section and a wide section. Also, in one embodiment the lateral spacing between the leaves is in the range of 125-12 microns. If the spacing is too great then there can be unwanted radiation leakage between the leaves, and if the spacing is too close there can be mechanical interference between leaves. In one embodiment the leaves are composed of a tungsten composite material.

The leaves include one type of leaf which is referred to as a target side leaf. Leaf 406 is an example of a target side leave. The target side leaf provides that the thicker part of the leaf, and, its hook element, are directed toward the radiation source side of the MLC. A second type of leave is an isocenter leave 408, where the isocenter leave has its thicker part and its hook element directed toward the patient side of the MLC. The arrangement of the leaves provides that the orientation of the leaves tends to point toward the radiation source. By inclining the position of the leaves relative to the source, the quality of the radiation shaping at the isocenter is improved.

It should be noted that the number of leaves used could vary depending on the specific implementation of MLC. For example, in one embodiment approximately 60 leaves are used on each side of the MLC, with about 30 high resolution leaves in the center area of the MLC and about 15 lower resolution leaves on the either side of the center area. In one embodiment the leaves of the MLC will have a length of approximately 205 mm, and height of 67 mm, with thickness dimensions as described below.

FIGS. 5A-5C show additional views of the leaves. FIG. 5A shows an isometric view of a target side leaf 502. The elongated arm 504 is provided to support the leaf 502 when the leaf is projected out from the support carriage. The length L2 in one embodiment of the MLC leave is in the range of 205 mm. The screw drive can be coupled to the inside body 506 of the leaf 502. FIG. 5B shows an end view of a target side leaf, and FIG. 5C shows an end view of an isocenter side leaf 508 as viewed from the drive end. It is noted that while the lateral sides of the thick portions of the leaves shown in FIGS. 5B and 5C appear to be parallel to each other, they are actually inclined relative to each other at approximately 0.5 degree. This inclined shape has been found to improve the imaging of the MLC. More specifically, the trapezoidal cross section of the leaf operates to minimize the side penumbra (shadows cast from the leaf sides). The incline on the lateral sides of the leaves points toward the radiation source.

The table below gives some exemplary dimensions of an embodiment herein, where the source is 1000 mm from the isocenter, and the horizontal centerline of the MLC is 510 mm from the source, providing a centerline clearance of 490 mm.

| Leaf type/Size | Average projected width at isocenter (patient treatment plane) (cm) | Average width at elevation of leaf (this is the middle point (W1) where the leave is transitioning from thin to thick) | Thick dimension, at thick part of leaf (cm) (this is measured between the top corners (W2) of the leaf) | Thin dimension at thin part of leave (cm) (this is measured at the bottom corners (W3) of the leaf) |
|---|---|---|---|---|
| Quarter target leaf (high resolution) | .25 | .125 | .15 | .09 |
| Quarter isocenter leaf (high resolution) | .25 | .125 | .17 | .07 |
| Half target leaf (low resolution) | .5 | .25 | .27 | .22 |
| Half isocenter leaf (low resolution) | .5 | .25 | .30 | .20 |

The fact that the leaves are shaped with a thin portion and thick portion allows for an overlap between the lateral sides of adjacent leafs. This overlap then operates to block the radiation, such that radiation can be selectively blocked by the MLC; thereby allowing for the shaping of the radiation field applied to the patient tissue at the isocenter. It should also be noted that the dimensions herein provide for a certain amount of blocking of radiation for a given leaf thickness dimension. For example, in an embodiment herein, a leaf thickness of 0.125 cm would provide approximately 0.25 cm shielding of radiation at the isocenter, when the isocenter is 1 meter from the source, and the center of the MLC is 510 mm from the source. However, if the MLC were positioned further away from the radiation source and closer to the isocenter then the amount of radiation shielding provided by the 0.125 cm thick leaf would be less than 0.25 cm. Thus, the projected resolution step at the isocenter is a function of both the thickness of the leaf, and the position of the leaf relative to the isocenter and the radiation source. Thus, one system could provide for very high resolution steps at the isocenter by positioning the leaves very close to the patient, but this can create a problem logistically, because there are big patients and there are various positioning devices that need sufficient clearance between the isocenter and the bottom of the MLC. As the distance is increased by moving the leaves up away from the patient, better clearance is obtained, but the leaves have to become much thinner to achieve the same projected dimension. An embodiment herein utilizes an MLC having leaves with a thickness sufficient to achieve high step resolution, such as 0.25 cm, and still provide for a clearance of in the range of 400 mm or greater, between the lowest surface of a structure including imaging components (typically the bottom of the MLC will be at, or very close to, this position) and the isocenter. Thus, an embodiment herein provides for a balance between the need to provide for good clearance above the patient, and still provide for a high step resolution.

Referring back to the discussion above regarding the screw motors of the MLC, the screw motors can utilize a screw having a diameter of about 1.2 mm. This screw can then be secured against the back of the corresponding leaf, and as the motor spins then it is either projected or retracted. The leaf drive screw motors are coupled to a precision gearbox and accompanying encoder; the configuration should provide for high precision motors so that the leaf's position can be precisely controlled. Additionally, the screw motors can be provided with a tunable axial clutch component. The tunable axial clutch component is responsive to the amount of axial force being applied to the screw, and if the applied force reaches a threshold amount, then the clutch will operate to disengage the motor from the screw, such that the axial force in excess of a threshold amount is not applied to the screw, and thus force in excess of a prescribed amount is not applied to force the projection of the corresponding leaf. This tunable axial clutch type of operation can be achieved using a spring loaded spline type device, and other fault tolerant drive train type implementations could be used. It can be very advantageous to employ some type of drive system which limits the amount of pressure applied to the MLC leaves, so that the leaves do not become damaged due the application of excessive force. This is particularly true in connection with the thinner high resolution leaves.

Referring back to FIG. 3A, reference is made to elements 310. Elements 310 provide for a plurality of circuit traces which provide for sensing the position of the various leaves of the MLC. These circuit traces can provide for a potentiometer type of device which uses electrical field information to determine the position of each of the leaves. The screw motors can also be used to mechanically sense the position of the leaves. Thus, two independent measures can be used to determine the position of the leaves of the MLC. Positional information can be transmitted via control lines to the computer 138.

In one embodiment of a radiation treatment system herein the system could provide for radiation treatment at any location within an area of 22×40 cm2. In such an embodiment if all of the leaves of the MLC are fully retracted then the area to which the radiation would be applied would be 22×40 cm2. In another embodiment a larger field of in the range of 26×40 cm2 could be provided. Indeed a range of different field sizes could be provided for.

Figure 6A:
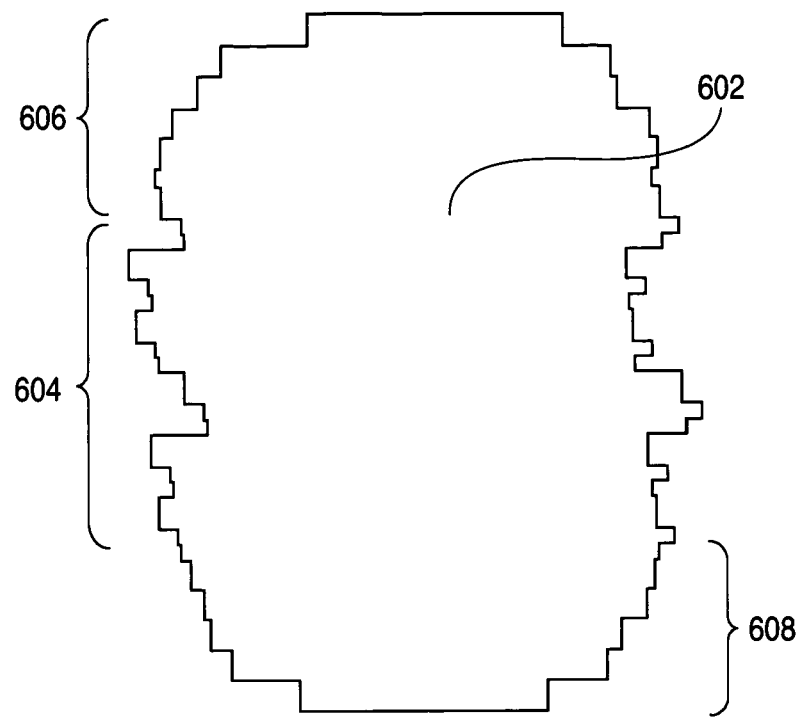
FIGS. 6A-6D show different views of projected radiation images, a dosimetry matrix, and illustrate the positioning of the MLC leaves for the corresponding projected radiation image.

FIG. 6A illustrates an area 602 which corresponds to a shape of a radiation energy field that could be projected on to a selected area of tissue for treatment located at the isocenter. In one embodiment, as shown in FIG. 6A, the radiation shape 602 has center area 604 which has first step resolution. In one embodiment this first step resolution will be a higher step resolution, then the step resolution provided in the areas 606 and 608 which area adjacent to the center area 604. The step resolution is determined in part by the thickness of the leaves of the MLC. Thus, for an MLC which has thinner, high resolution leaves in a center area of the MLC, the shape will have higher step resolution in the center area than on the sides of the image which correspond to the leaves of the MLC which are thicker, lower resolution leaves.

Figure 6B:
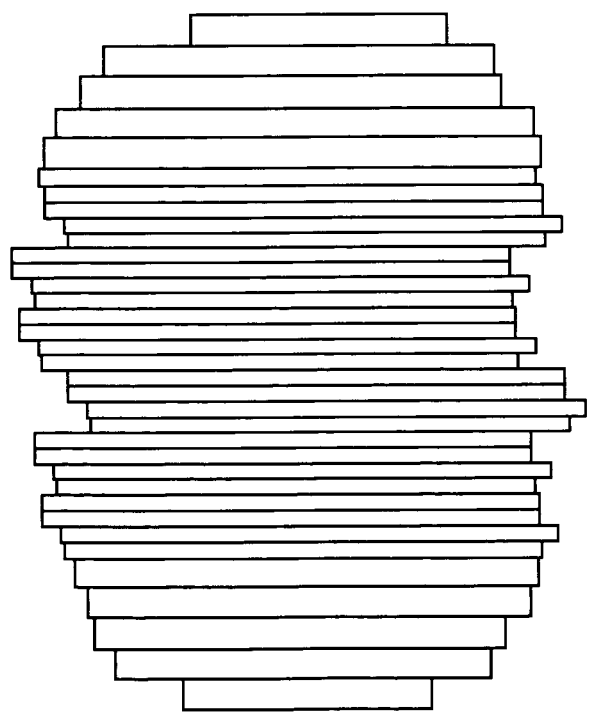

FIG. 6B illustrates the area 602, but with rectangular images laid over the projected radiation shape 602. These rectangular images illustrate the area of the image that would correspond to areas defined by the retraction of the leaves of an MLC, and also make it easier to recognize the high resolution area 604 of the shape versus the low resolution areas of the shape 606 and 608.

Figure 6C:
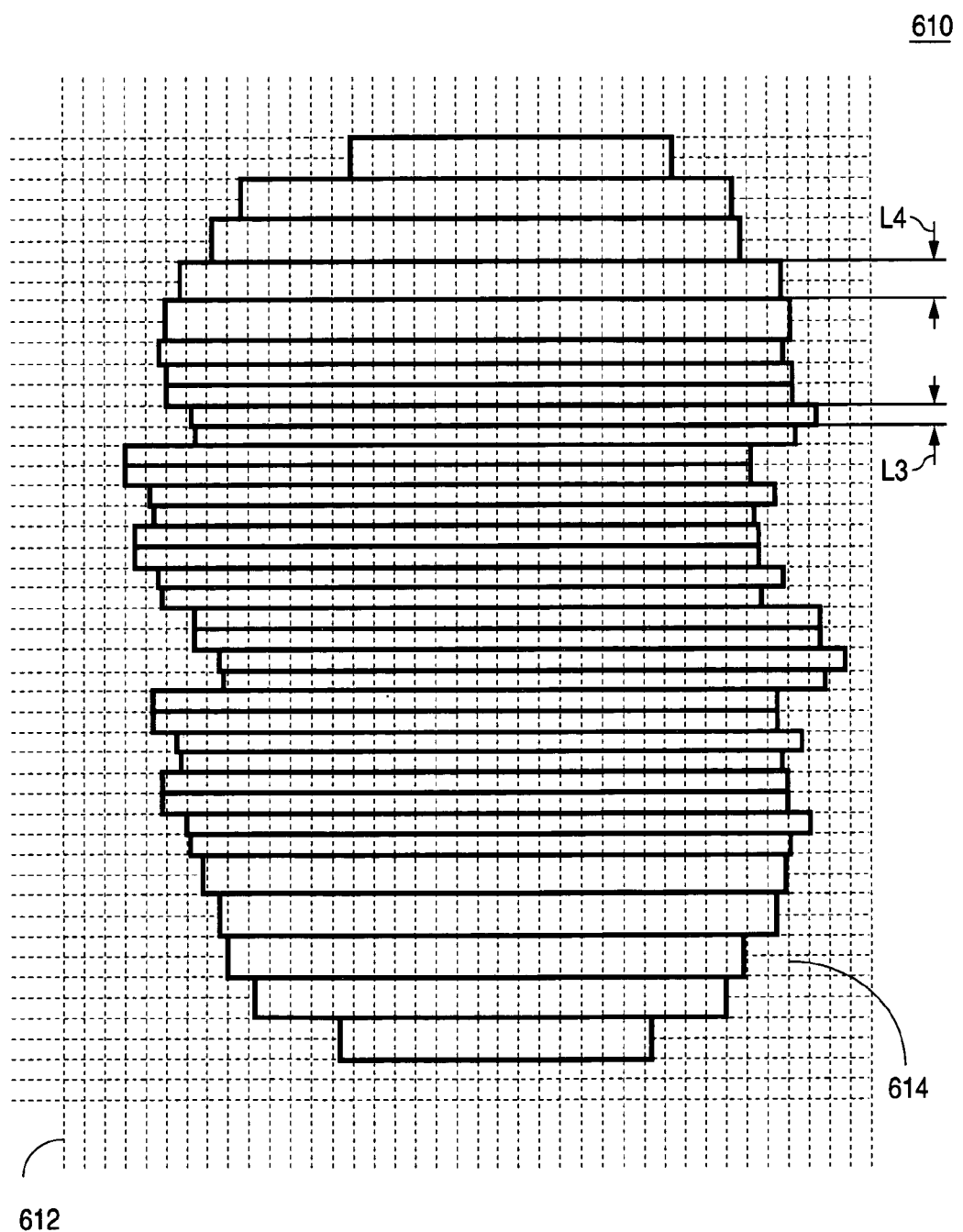

FIG. 6C shows illustrates an image, or screen shot, 610 which could be shown on a display of a computer as previously discussed in connection with FIG. 1B. In operation a doctor or other medical provider using the radiation treatment system, would have information to identify the shape and position of the area of tissue to be treated. This information can be used by the computer of the radiation treatment system to determine the positioning of leaves of the MLC, so that the leaves will block some portion of the radiation energy emitted by the energy source, and allow another portion of the radiation energy to be transmitted through the MLC and be incident on the tissues to be treated at the isocenter. In one embodiment of the system herein, as part of this treatment operation the operator of the system will review the corresponding area of the projected image as shown on the computer display. The operator can use the user interface control to make specific adjustments to the MLC leaves to change the position of the leaves, and the corresponding projected image will change. In providing for radiation treatment, it can be important to precisely determine the total tissue area to which the radiation is applied, and the location of the tissue to which the radiation is applied. In connection with tracking the area of tissue to which the radiation is applied, a dosimetry matrix, also referred to as a dose calculation matrix can be used. FIG. 6C illustrates a dose calculation matrix 612 which could be used in an embodiment herein. The dose calculation matrix 612 provides for units, which are shown as grid squares 614 in FIG. 6C. By determining the number of units of area that the projected radiation will cover in the dose calculation matrix 612, the amount of radiation applied to the patient's tissue can be determined. In one embodiment of a system according to the invention herein, the dose calculation matrix will have a unit length, as determined by the side of one of the unit squares which would correspond to the projected step resolution of the high resolution leaves of the MLC.

For example, the displayed step resolution length L3 shown in FIG. 6C corresponds to the length of the dose calculation matrix unit. In one embodiment the displayed step resolution L3 could, instead of being the same as the length of the dose calculation matrix unit length, be a whole number integer of the matrix unit length. In the embodiment shown in FIG. 6C, the displayed step resolution length L4 in one of the lower resolution areas of projected images would be whole number integer multiple of the of the matrix unit length. In the case shown the lower resolution area of the step resolution is twice the length of the higher step resolution area. In one embodiment a first area of the actual projected image at the isocenter will have a step resolution of 3 mm or less, and the dose calculation matrix unit length will correspond to the step resolution of the first area of the projected image at isocenter. In one embodiment the step resolution of the first area of the actual image at the isocenter will be approximately 2.5 mm, and the dose calculation matrix unit length will correspond to the approximately 2.5 mm. This step resolution and matrix unit length value and relationship works well because it provides a user with the a step resolution unit value which is intuitive, and easy for the user to do simple calculations, in part because the unit value divides evenly into the value of 10, which means that for example four units at 2.5 mm will equal 10 mm, or 1 cm.

Figure 6D:
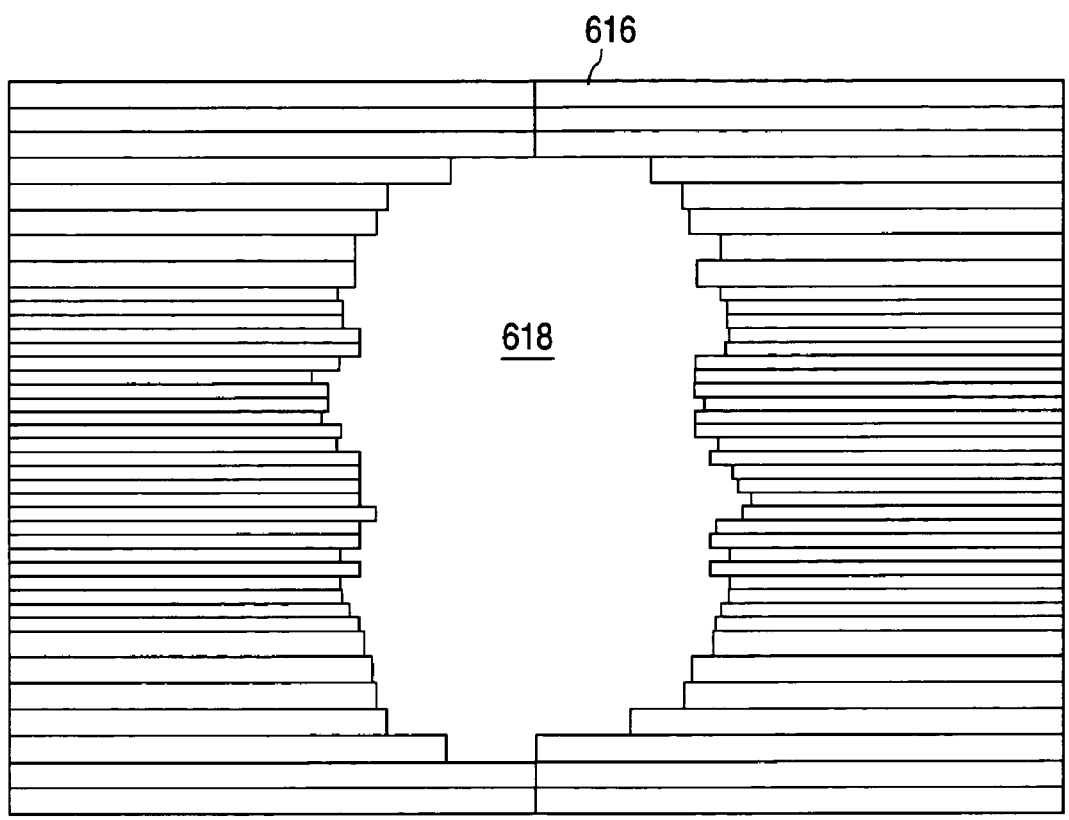

FIG. 6D is simplified illustration of the positioning of the leaves 616 of an MLC, to provide a projected radiation shape which would correspond to the image 602 as shown FIGS. 6A-6C. The positioning of the leaves operates to block the emitted radiation which is directed to the area occupied by the leaves, and the combined positioning of all the leaves operates to define a space 618 through which emitted radiation passes, and this space 618 operates to define the shape of the projected radiation image which is incident at the isocenter. In the embodiments described above the MLC provides for center area with high resolution leaves, and outer areas with lower resolution leaves. Additionally, MLC embodiments could include additional leaves having different thicknesses which would provide for still lower resolution steps in the projected radiation shape at the isocenter.

It should be noted that the above descriptions illustrate certain embodiments for illustrative purposes and one of skill in the art would recognize that specific implementations of the invention herein could be implemented in different ways. Thus, while various embodiments of the present invention have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Thus, the present invention should not be limited by any of the above-described exemplary embodiments, but should be defined only in accordance with the following claims and their equivalents.

What is claimed is:

1. A radiation treatment system including:
   a radiation source which emits radiation energy;
   a multi-leaf collimator positioned between the radiation source and an isocenter, such that a portion of the radiation energy from the radiation source is transmitted through the multi-leaf collimator to the isocenter;
   wherein the multi-leaf collimator includes a plurality of leaves, each leaf being movable to allow a selected portion of the radiation energy to be blocked, whereby a shape is defined by the portion of radiation energy which is incident at the isocenter, and the shape is controlled by a positioning of the plurality of leaves; and
   wherein the multi-leaf collimator includes a first set of leaves which provide for a first area of the shape that has a step resolution length in the range of approximately 3.0 mm or less and wherein the multi-leaf collimator is positioned such that there is a clearance in range approximately 400 mm or greater between the multi-leaf collimator and the isocenter; and
   wherein the step resolution length corresponds to a length dimension of a dose calculation matrix.

2. The radiation system of claim 1 wherein the step resolution length is approximately 2.5 mm.

3. The radiation treatment system of claim 1, wherein a widest point in the first set of leaves is no greater than about 1.7 mm.

4. The radiation treatment system of claim 3, wherein the plurality of leaves includes a second set of leaves wherein a widest point in second set of leaves is no greater than about 3 mm.

5. The radiation treatment system of claim 1, wherein one or more of the leaves of the multileaf collimator has a stroke length of about 205 mm or greater.

6. The radiation treatment system of claim 1, wherein the shape defined by the portion of radiation energy provides a treatment area about $22 \times 40$ cm$^2$ or greater.

7. A radiation treatment system including:
   a radiation source which emits radiation energy;

a multi-leaf collimator positioned between the radiation source and an isocenter, such that a portion of the radiation energy from the radiation source is transmitted through the multi-leaf collimator to the isocenter;

wherein the multi-leaf collimator includes a plurality of leaves, each leaf being movable to allow a selected portion of the radiation energy to be blocked, whereby a shape is defined by the portion of radiation energy which is incident at the isocenter, and the shape is controlled by a positioning of the plurality of leaves; and wherein the multi-leaf collimator includes a first set of leaves which provide for a first area of the shape that has a step resolution length in the range of approximately 3.0 mm or less and wherein the multi-leaf collimator is positioned such that there is a clearance in range approximately 400 mm or greater between the multi-leaf collimator and the isocenter; and wherein the step resolution length corresponds to a whole number integer multiple of a unit length dimension of a dose calculation matrix.

8. A radiation treatment system including:

a radiation source which emits radiation energy;

a multi-leaf collimator positioned between the radiation source and an isocenter, such that a portion of the radiation energy from the radiation source is transmitted through the multi-leaf collimator to the isocenter;

wherein the multi-leaf collimator includes a plurality of leaves, each leaf being movable to allow a selected portion of the radiation energy to be blocked, whereby a shape is defined by the portion of radiation energy which is incident at the isocenter, and the shape is controlled by a positioning of the plurality of leaves; and wherein the multi-leaf collimator includes a first set of leaves which provide for a first area of the shape that has a step resolution length in the range of approximately 3.0 mm or less and wherein the multi-leaf collimator is positioned such that there is a clearance in range approximately 400 mm or greater between the multi-leaf collimator and the isocenter; and wherein the step resolution length corresponds to a length dimension of a dose calculation matrix, and wherein the multi-leaf collimator includes a second set of leaves which provide for a second area of the shape that has a second step resolution length, and the second step resolution length corresponds to a whole number integer multiple of the length dimension of the dose calculation matrix, and the whole number integer is a number greater than one.

9. The radiation treatment system of claim 8, wherein the first step resolution length is about 2.5 mm, and the second step resolution length is about 5 mm.

10. A radiation treatment system including:

a radiation source which emits radiation energy;

a multi-leaf collimator positioned between the radiation source and an isocenter, such that a portion of the radiation energy from the radiation source is transmitted through the multi-leaf collimator to the isocenter;

wherein the multi-leaf collimator includes a plurality of leaves, each leaf being movable to allow a selected portion of the radiation energy to be blocked, whereby a shape is defined by the portion of radiation energy which is incident at the isocenter, and the shape is controlled by a positioning of the plurality of leaves; and wherein at least a first area of the shape has a first step resolution length in the range of approximately 3.0 mm or less and, wherein the first step resolution length corresponds to a length dimension of a dose calculation matrix.

11. The radiation treatment system of claim 10, wherein the radiation source is positioned at a distance of approximately 800 mm or greater from the isocenter.

12. The radiation treatment system of claim 10, wherein the radiation source is positioned at a distance of approximately 1000 mm from the isocenter.

13. The radiation treatment system of claim 10 wherein the plurality of leaves includes a first set of leaves which have a maximum width provides for a step resolution length in the range of about 2.5 mm in at least the first area of the shape.

14. The radiation treatment system of claim 13 wherein the plurality of leaves include a second set of leaves having a second maximum width which provides for a step resolution length in the range of about 5 mm in a second area of the shape.

15. The radiation treatment system of claim 10 wherein at least a second portion of shape has a second step resolution length which is approximately twice the first step resolution length.

16. The radiation system of claim 15 wherein the first step resolution length is approximately 2.5 mm.

17. The radiation treatment system of claim 10, wherein a second area of the shape has a second step resolution length, and the second step resolution length corresponds to a whole number integer multiple of the length dimension of the dose calculation matrix, and the whole number integer is a number greater than one.

18. The radiation treatment system of claim 17, wherein the first step resolution length is about 2.5 mm, and the second step resolution length is about 5 mm.

19. The radiation treatment system of claim 10, wherein the plurality of leaves includes a first set of leaves wherein a widest point in first set of leaves is no greater than about 1.7 mm.

20. The radiation treatment system of claim 19, wherein the plurality of leaves includes a second set of leaves wherein a widest point in second set of leaves is no greater than about 3 mm.

21. The radiation treatment system of claim 10, wherein one or more of the leaves of the multileaf collimator has a stroke length of about 205 mm or greater.

22. The radiation treatment system of claim 10, wherein the shape defined by the portion of radiation energy provides a treatment area about 22×40 cm$^2$ or greater.

23. A radiation treatment system including:

a radiation source which emits radiation energy;

a multi-leaf collimator positioned between the radiation source and an isocenter, such that a portion of the radiation energy from the radiation source is transmitted through the multi-leaf collimator to the isocenter;

wherein the multi-leaf collimator includes a plurality of leaves, each leaf being movable to allow a selected portion of the radiation energy to be blocked, whereby a shape is defined by the portion of radiation energy which is incident at the isocenter, and the shape is controlled by a positioning of the plurality of leaves; and wherein at least a first area of the shape has a first step resolution length in the range of less than approximately 3.0 mm or less and the first step resolution length corresponds to a whole number integer multiple of a length dimension of a dose calculation matrix.

24. The radiation treatment system of claim 23, wherein the radiation source is positioned at a distance of approximately 800 mm or greater from the isocenter.

25. The radiation treatment system of claim 23, wherein the radiation source is positioned at a distance of approximately 1000 mm from the isocenter.

26. The radiation treatment system of claim 23, wherein the plurality of leaves includes a first set of leaves which have a maximum width provides for a step resolution length of approximately 2.5 mm in at least the first area of the shape.

27. The radiation treatment system of claim 26 wherein the plurality of leaves include a second set of leaves having a second maximum width which provides for a step resolution length of approximately 5 mm in a second area of the shape.

28. The radiation treatment system of claim 23 wherein at least a second area of the shape has a second step resolution length which is approximately twice the step resolution length of the first area of the shape.

29. The radiation treatment system of claim 23, wherein a second area of the shape has a second step resolution length, and the second step resolution length is a whole number integer multiple of the width dimension of the dose calculation matrix, and the whole number integer is a number greater than one.

30. The radiation treatment system of claim 29, wherein the first step resolution length is about 2.5 mm, and the second step resolution length is about 5 mm.

31. The radiation treatment system of claim 23 wherein the plurality of leaves includes a first set of leaves wherein a widest point in first set of leaves is about 1.7 mm or less.

32. The radiation treatment system of claim 31, wherein the plurality of leaves includes a second set of leaves wherein a widest point in second set of leaves is about 3 mm or less.

33. The radiation treatment system of claim 23, wherein one or more of the leaves of the multileaf collimator has a stroke length of about 205 mm or greater.

34. The radiation treatment system of claim 23, wherein the shape defined by the portion of radiation energy provides a treatment area about 22×40 cm$^2$ or greater.

* * * * *